(12) United States Patent
Gregorich et al.

(10) Patent No.: US 7,998,132 B2
(45) Date of Patent: Aug. 16, 2011

(54) ADJUSTABLE STIFFNESS CATHETER

(75) Inventors: Daniel J. Gregorich, St. Louis Park, MN (US); Soo-Young Yoon, Maple Grove, MN (US); Michael P. Meyer, Richfield, MN (US); Liza J. Davis, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1748 days.

(21) Appl. No.: 11/218,857

(22) Filed: Sep. 2, 2005

(65) Prior Publication Data
US 2007/0060880 A1 Mar. 15, 2007

(51) Int. Cl.
*A61M 25/00* (2006.01)

(52) U.S. Cl. ..................................................... 604/525

(58) Field of Classification Search ............... 604/264, 604/536, 523–525; 600/144, 152
See application file for complete search history.

(56) References Cited

U.S. PATENT DOCUMENTS

| | | | |
|---|---|---|---|
| 4,586,923 A | 5/1986 | Gould et al. | |
| 4,738,667 A | 4/1988 | Galloway | |
| 4,822,345 A | 4/1989 | Danforth | |
| 4,976,689 A | 12/1990 | Buchbinder et al. | |
| 5,228,453 A | 7/1993 | Sepet | |
| 5,423,771 A | 6/1995 | Imran | |
| 5,545,138 A | 8/1996 | Fugoso et al. | |
| 5,810,867 A | 9/1998 | Zarbatany et al. | |
| 6,030,405 A | 2/2000 | Zarbatany et al. | |
| 6,544,231 B1 | 4/2003 | Palmer et al. | |
| 6,562,021 B1 * | 5/2003 | Derbin et al. | 604/523 |
| 6,702,781 B1 | 3/2004 | Reifart et al. | |
| 6,733,473 B1 | 5/2004 | Reifart et al. | |
| 6,755,794 B2 | 6/2004 | Soukup | |
| 6,776,765 B2 | 8/2004 | Soukup et al. | |
| 7,575,807 B1 * | 8/2009 | Barvosa-Carter et al. | 428/411.1 |
| 2003/0212356 A1 * | 11/2003 | Scorvo | 602/20 |
| 2004/0054322 A1 * | 3/2004 | Vargas | 604/95.04 |
| 2005/0119614 A1 | 6/2005 | Melsky | |
| 2005/0165439 A1 * | 7/2005 | Weber et al. | 606/191 |
| 2006/0192465 A1 * | 8/2006 | Kornbluh et al. | 310/800 |

FOREIGN PATENT DOCUMENTS

WO 97/09924 A1 3/1997

* cited by examiner

*Primary Examiner* — Theodore J Stigell

(74) *Attorney, Agent, or Firm* — Seager, Tufte & Wickhem LLC

(57) ABSTRACT

Medical devices such as catheters can include structure or provision that permit a physician or other health care professional to adjust the stiffness of at least a portion of the medical device. In some instances, the medical device may be adjusted prior to inserting the medical device into a patient. In some cases, the medical device may be adjusted while in use within the patient.

5 Claims, 16 Drawing Sheets

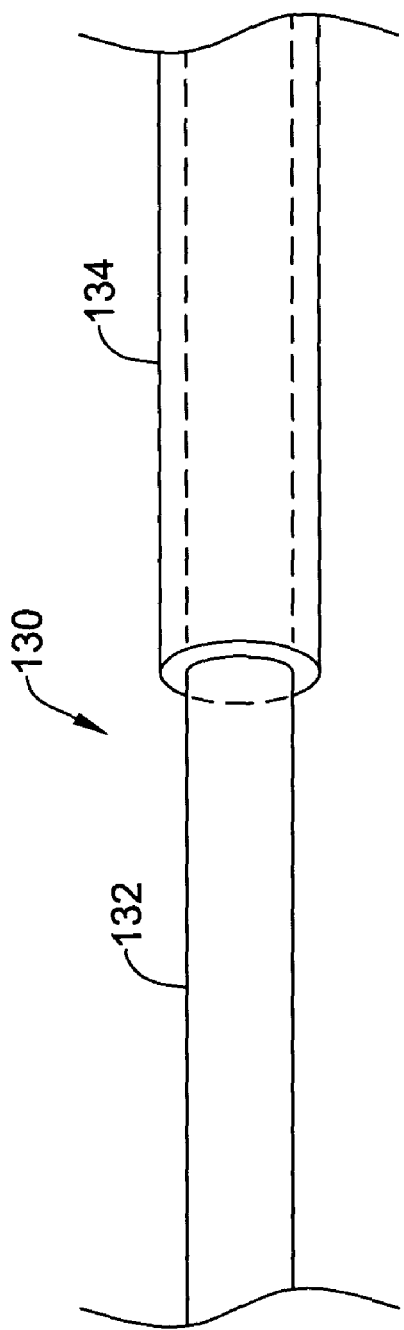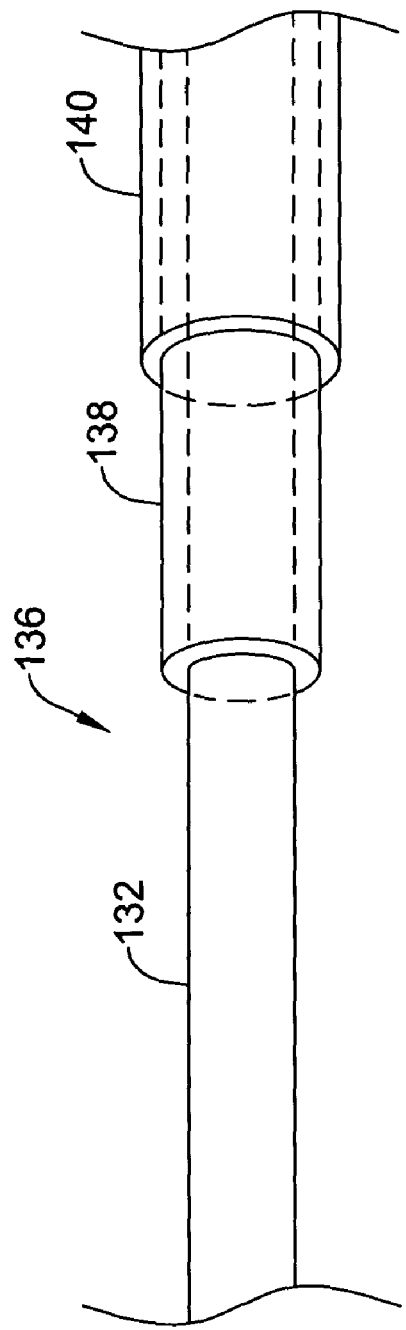
Figure 15
Figure 16

ADJUSTABLE STIFFNESS CATHETER

TECHNICAL FIELD

The invention relates generally to medical devices such as catheters and relates more particularly to catheters that include structure or provision providing adjustable stiffness.

BACKGROUND

Medical devices such as catheters may be subject to a number of often conflicting performance requirements such as flexibility and strength. In some instances, improved flexibility may come at the expense of reduced strength. Increased strength may come at the expense of reduced flexibility. Because each patient is unique, there may be a unique balance of performance parameters such as flexibility and strength optimal for a particular patient.

While it would certainly be possible to construct a large number of catheters, to accommodate any feasible set of desired performance parameters, this would likely be cost-prohibitive. Moreover, in some instances, a physician may determine in the middle of a procedure that a particular balance of stiffness versus flexibility may be necessary. Therefore, a need remains for medical devices such as catheters that may be adjusted, particularly in situ, with respect to their stiffness.

SUMMARY

The invention pertains generally to medical devices such as catheters that include structure or provision that permit a physician or other health care professional to adjust the stiffness of at least a portion of the medical device. In some instances, the medical device may be adjusted prior to inserting the medical device into a patient. In some cases, the medical device may be adjusted while in use within the patient.

Accordingly, an example embodiment of the invention can be found in an adjustable catheter that includes an elongate polymeric shaft extending from a proximal region of the catheter to a distal region of the catheter and a first spiral-cut hypotube that is disposed within the elongate polymeric shaft.

Another example embodiment of the invention can be found in an adjustable catheter having an elongate polymeric shaft defining a lumen that extends from a proximal region of the catheter to a distal region of the catheter. A first inflatable tube that extends from the proximal region to the distal region and that is arranged at least substantially parallel with a longitudinal axis of the catheter is disposed within the lumen. Inflating the first inflatable tube causes the elongate polymeric shaft to increase in stiffness.

Another example embodiment of the invention can be found in an adjustable catheter that includes an inner polymeric liner, an outer polymeric liner, and a swellable layer disposed between the inner polymeric liner and the outer polymeric liner. Adding an appropriate fluid to the swellable layer increases the stiffness of the adjustable catheter.

Another example embodiment of the invention can be found in an adjustable catheter having an elongate polymeric shaft that extends from a proximal region to a distal region of the catheter. A stiffness-enhancing sheath that is more stiff than the elongate polymeric shaft is slidably disposed over the elongate polymeric shaft.

Another example embodiment of the invention can be found in an adjustable catheter that includes an elongate polymeric shaft that extends from a proximal region of the catheter to a distal region of the catheter and that includes a wall. A number of elongate apertures are disposed within the wall such that they extend longitudinally within the elongate polymeric shaft. Each of a number of stiffness-enhancing filaments are slidably disposed in each of the number of elongate apertures.

Another example embodiment of the invention can be found in an adjustable catheter having an inner polymeric layer that includes one or more electrically actuated stiffness enhancers. An outer polymeric layer is disposed over the inner polymeric layer.

Another example embodiment of the invention can be found in an adjustable catheter that includes an elongate polymeric shaft having a stiffness. The stiffness of the elongate polymeric shaft can be changed by applying a current to the elongate polymeric shaft.

The above summary of the present invention is not intended to describe each disclosed embodiment or every implementation of the present invention. The Figures, Detailed Description and Examples which follow more particularly exemplify these embodiments.

BRIEF DESCRIPTION OF THE FIGURES

The invention may be more completely understood in consideration of the following detailed description of various embodiments of the invention in connection with the accompanying drawings, in which:

FIG. 15 is a side elevation view of a catheter in accordance with an embodiment of the invention;

FIG. 16 is a side elevation view of a catheter in accordance with an embodiment of the invention;

Figure 1:
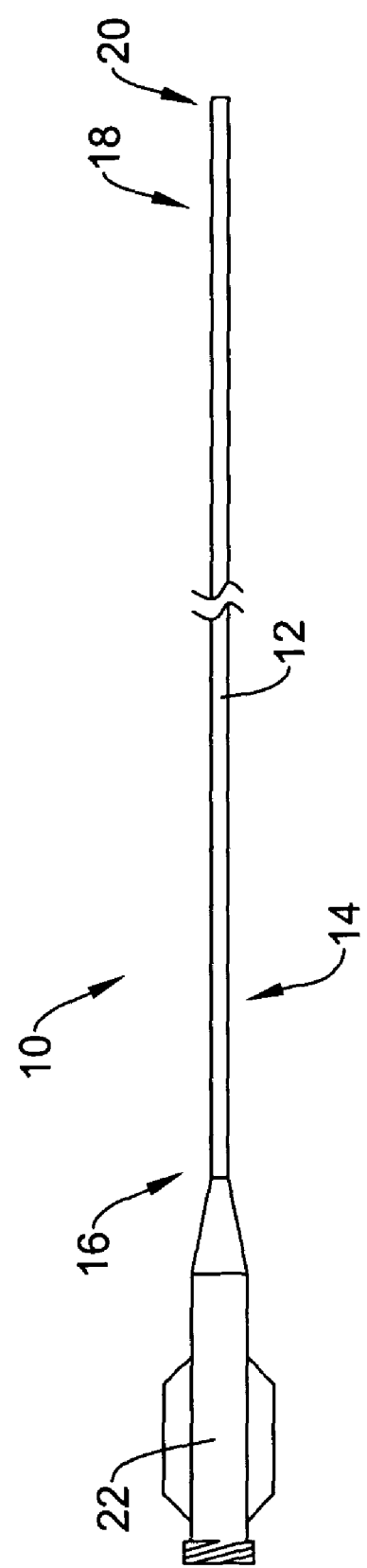
FIG. 1 is a side elevation view of a catheter in accordance with an embodiment of the invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following description should be read with reference to the drawings wherein like reference numerals indicate like elements throughout the several views. The drawings, which are not necessarily to scale, depict illustrative embodiments of the claimed invention.

FIG. 1 is a plan view of a catheter 10 in accordance with an embodiment of the present invention. The catheter 10 can be any of a variety of different catheters. In some embodiments, the catheter 10 can be an intravascular catheter. Examples of intravascular catheters include balloon catheters, atherectomy catheters, drug delivery catheters, stent delivery catheters, diagnostic catheters and guide catheters. The intravascular catheter 10 can be sized in accordance with its intended use. The catheter 10 can have a length that is in the range of about 100 to 150 centimeters and can have any useful diameter. As illustrated, FIG. 1 portrays a guide catheter, but the invention is not limited to such. Except as described herein, the intravascular catheter 10 can be manufactured using conventional techniques.

In the illustrated embodiment, the intravascular catheter 10 includes an elongate shaft 12 that has a proximal region 14 defining a proximal end 16 and a distal region 18 defining a distal end 20. A hub and strain relief assembly 22 can be connected to the proximal end 16 of the elongate shaft 12. The hub and strain relief assembly 22 can be of conventional design and can be attached using conventional techniques. It is also recognized that alternative hub designs can be incorporated into embodiments of the present invention.

The elongate shaft 12 can include one or more shaft segments having varying degrees of flexibility. For example, the elongate shaft may include a relatively stiff proximal portion, a relatively flexible distal portion and an intermediate position disposed between the proximal and distal portions having a flexibility that is intermediate to both.

In some cases, the elongate shaft 12 may be formed of a single polymeric layer. In some instances, the elongate shaft 12 may include an inner liner such as an inner lubricious layer and an outer layer. In some cases, the elongate shaft 12 may include a reinforcing braid layer disposed between the inner and outer layers. The elongate shaft 12 is considered herein as generically representing a catheter to which various elements can be added to provide the catheter 10 with adjustable stiffness.

If the elongate shaft 12 includes an inner liner, the inner liner can include or be formed from a coating of a material having a suitably low coefficient of friction. Examples of suitable materials include perfluoro polymers such as polytetrafluoroethylene (PTFE), better known as TEFLON®, high density polyethylene (HDPE), polyarylene oxides, polyvinylpyrolidones, polyvinylalcohols, hydroxy alkyl cellulosics, algins, saccharides, caprolactones, and the like, and mixtures and combinations thereof.

The elongate shaft 12 can include, as an outer layer or layers, any suitable polymer that will provide the desired strength, flexibility or other desired characteristics. Polymers with low durometer or hardness can provide increased flexibility, while polymers with high durometer or hardness can provide increased stiffness. In some embodiments, the polymer material used is a thermoplastic polymer material. Some examples of suitable materials include polyurethane, elastomeric polyamides, block polyamide/ethers (such as PEBAX®), silicones, and co-polymers. The outer polymer layer 32 can be a single polymer, multiple longitudinal sections or layers, or a blend of polymers. By employing careful selection of materials and processing techniques, thermoplastic, solvent soluble, and thermosetting variants of these materials can be employed to achieve the desired results. In some instances, a thermoplastic polymer such as a co-polyester thermoplastic elastomer, for example, available commercially under the ARNITEL® name, can be used.

Figure 2:
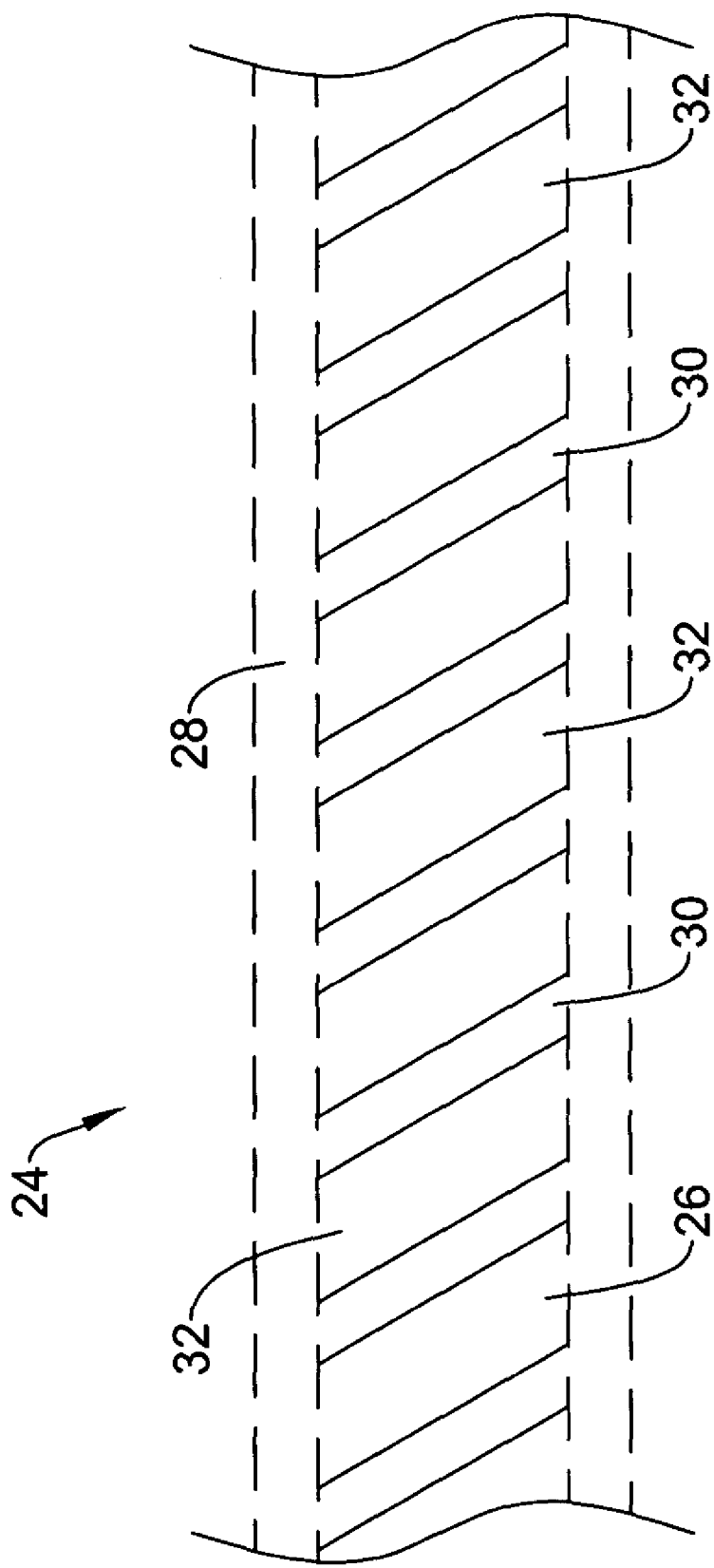
FIG. 2 is a diagrammatic longitudinal cross-section of a portion of a catheter in accordance with an embodiment of the invention.

FIG. 2 illustrates an assembly 24 that includes a hypotube 26 disposed within a polymeric layer 28. Merely for illustrative purposes, the polymeric layer 28 is seen in phantom as a single layer. In some cases, the polymeric layer 28 may represent two or more polymer layers. Any suitable polymers may be employed. It is contemplated that the assembly 24 could also include one or more polymeric layers, such a lubricious layer, within the hypotube 26.

The hypotube 26 can be cut for flexibility purposes. In some instances, such as that illustrated, the hypotube 26 can be a spiral-cut hypotube having spirally-aligned cuts or kerfs 30 separating adjacent bridge portions 32. The bridge portions 32 permit the hypotube 26 to retain a certain level of strength while the kerfs 30 lend flexibility. The hypotube 26 can be formed of any suitable polymeric or metallic material. In some instances, the hypotube 26 can be formed of stainless steel that has been laser cut.

Each of the kerfs 30 can be seen to have a particular width. FIG. 2 can be assumed as showing the hypotube 26 in a relaxed configuration, i.e. no external forces are being applied to the hypotube 26. The relative dimensions of the kerfs 30 and the bridge portions 32 will provide the hypotube 26, and hence, the assembly 24, with a given balance of flexibility versus strength.

Figure 3:
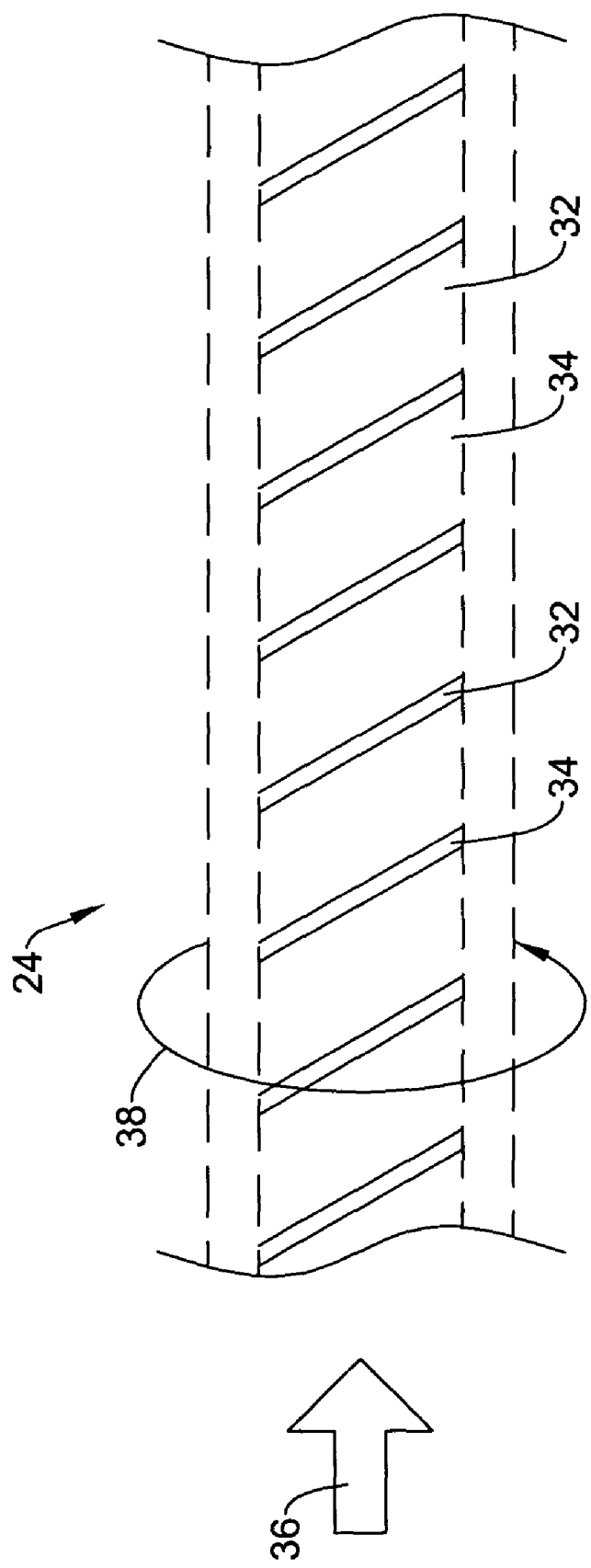
FIG. 3 is a diagrammatic longitudinal cross-section of a portion of the catheter of FIG. 2.

In FIG. 3, the assembly 24 has been stiffened by reducing the relative size of each of the kerfs 34 while each of the bridge portions 32 remain unchanged. This can be accomplished by, for example, applying a compressive force to the hypotube 26, as shown by arrow 36. Alternatively, this can also be accomplished by rotating the hypotube 26, as shown by arrow 38. While not expressly illustrated, it should be recognized that applying either a compressive or rotational force to the hypotube 26 may change the diameter of the hypotube 26.

Figure 4:
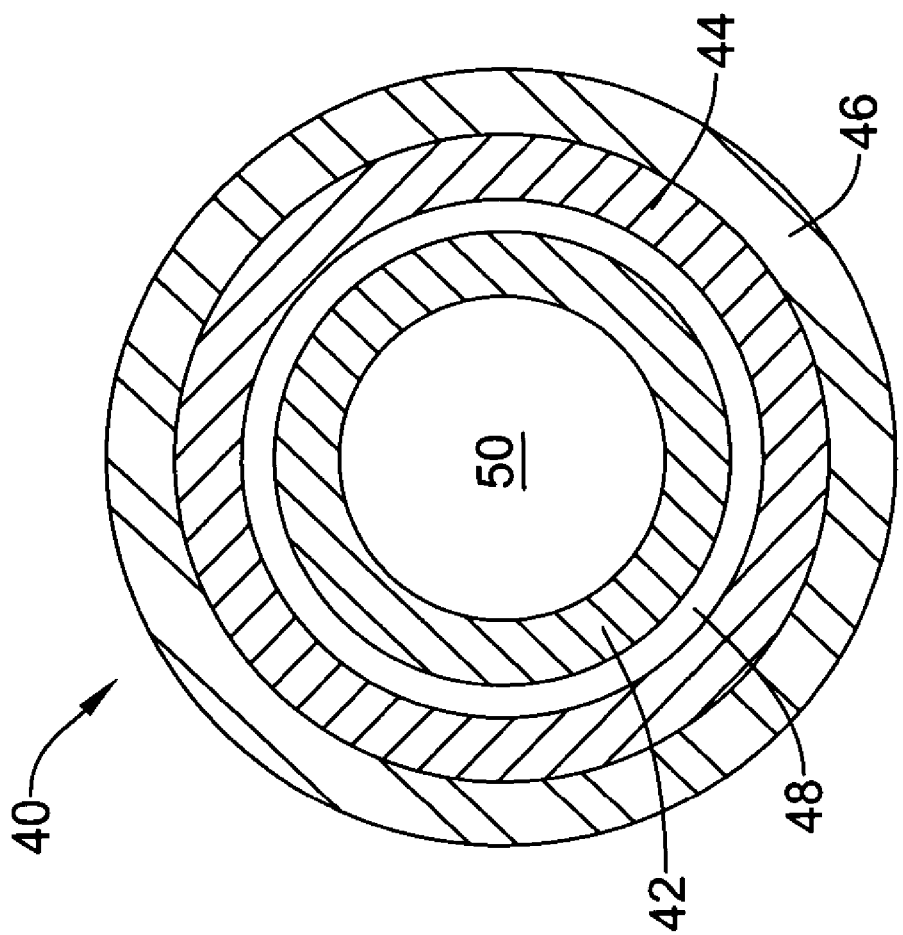
FIG. 4 is a diagrammatic cross-section of a catheter in a relaxed configuration, in accordance with an embodiment of the invention.
Figure 5:
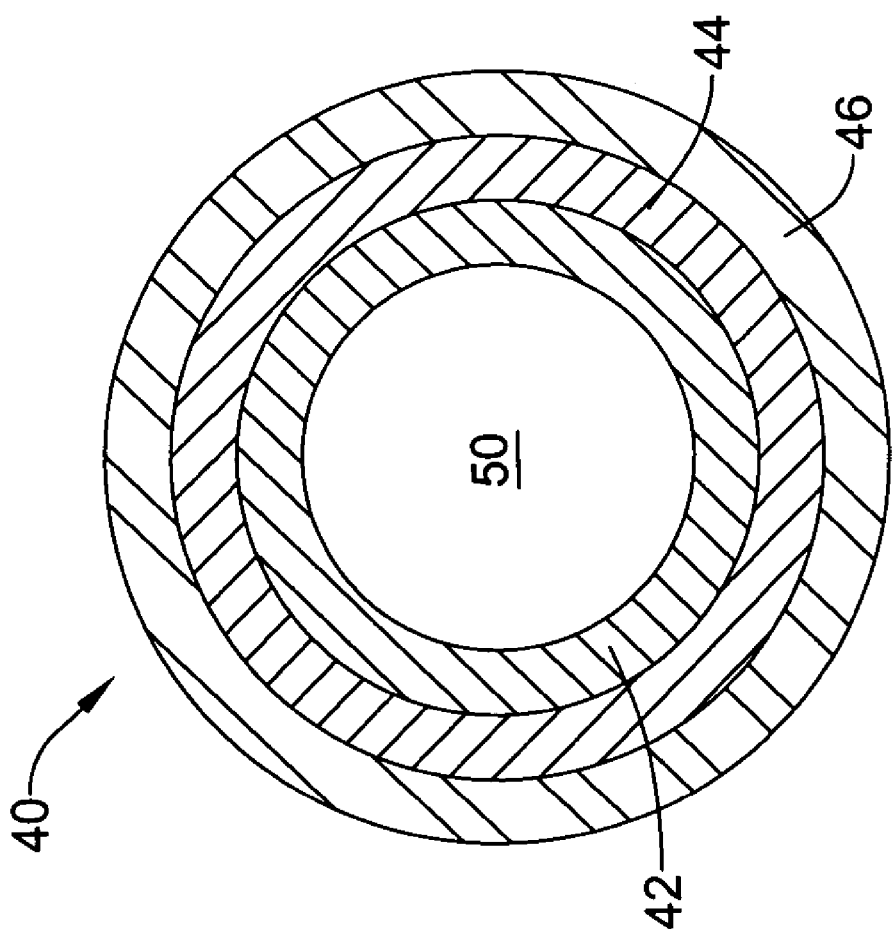
FIG. 5 is a view of the catheter of FIG. 4.
Figure 6:
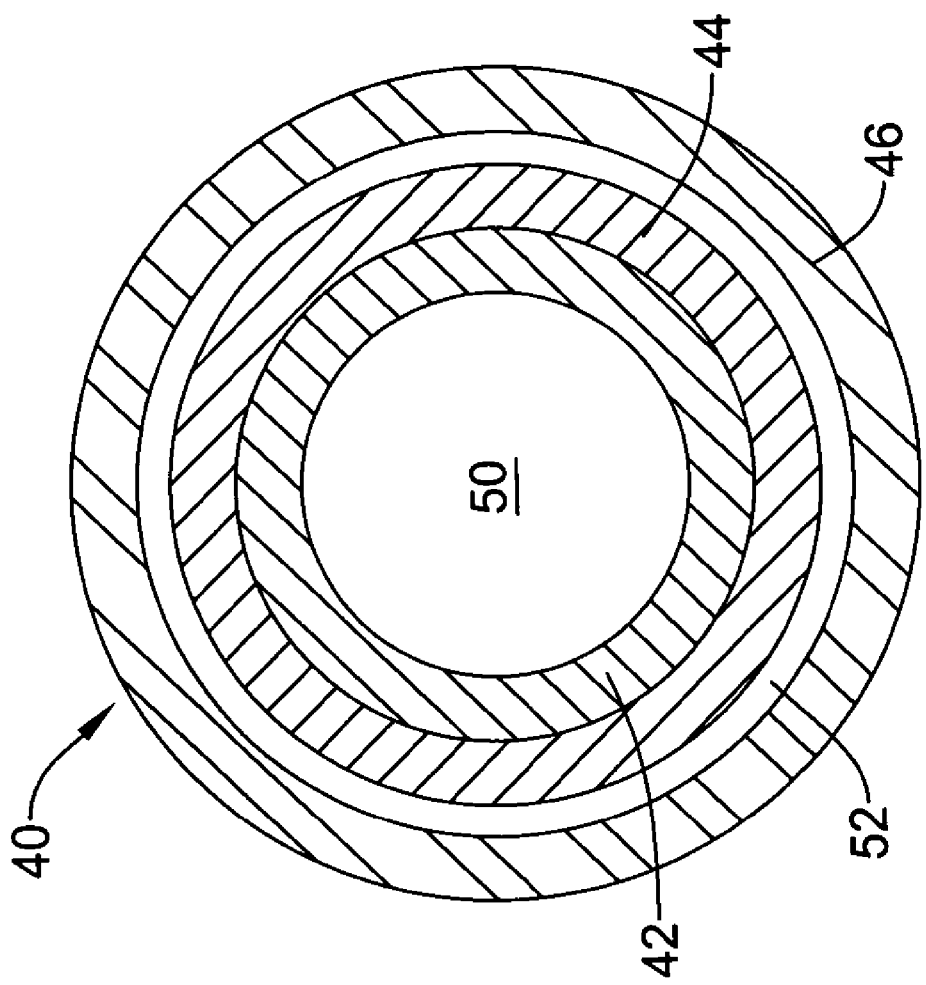
FIG. 6 is another view of the catheter of FIG. 4.

In some instances, as seen for example in FIGS. 4-6, a catheter may include two or more coaxially aligned hypotubes. FIG. 4 is a diagrammatic cross-section of an assembly 40, showing an inner hypotube 42, an outer hypotube 44 and a polymeric layer 46. The polymeric layer 46 can be formed of any suitable polymer. While not expressly illustrated as such, the inner hypotube 42 and the outer hypotube 44 may both be spirally-cut. The inner hypotube 42 and the outer hypotube 44 can each be formed of any suitable polymeric or metallic material. In some instances, the inner hypotube 42 and the outer hypotube 44 can each be formed of stainless steel that has been laser cut.

An annular gap 48 can be seen between the inner hypotube 42 and the outer hypotube 44. It should be noted that FIG. 4 is not to scale; rather, certain elements have been exaggerated for clarity. The inner hypotube 42 can be considered as having an outer diameter that is somewhat less than an inner diameter of the outer hypotube 44. The inner hypotube 42, along with any desired inner layer or layers (not illustrated), forms a lumen 50 suitable for any desired or necessary medical treatment.

It will be recognized that the annular gap 48 will permit at least some relative movement between the inner hypotube 42 and the outer hypotube 44 before interference between the two will decrease flexibility of the assembly 40. FIG. 4 can be considered as illustrating a relaxed configuration, i.e. no external forces are being applied to any portions of the assembly 40.

In FIG. 5, however, the inner hypotube 42 has expanded relative to the outer hypotube 44 such that the annular gap 48 (seen in FIG. 4) has at least substantially disappeared. This can be accomplished, for example, by rotating the inner hypotube 42 to expand the diameter of the inner hypotube 42. In some instances, the inner hypotube 42 may extend proximally to the proximal region 14 (see FIG. 1), or may be operatively connected to actuation structure that extends proximally to the proximal region 14, to permit an operator to rotate the inner hypotube 42.

Conversely, as shown in FIG. 6, the outer hypotube 44 may be contracted in diameter relative to the inner hypotube 42 such that a new annular gap 52 appears between the outer hypotube 44 and the polymeric layer 46. This can be accomplished, for example, by rotating the outer hypotube 44 to decrease the diameter of the outer hypotube 44. In some instances, the outer hypotube 44 may extend proximally to the proximal region 14 (see FIG. 1), or may be operatively connected to actuation structure that extends proximally to the proximal region 14, to permit an operator to rotate the outer hypotube 44.

Figure 7:
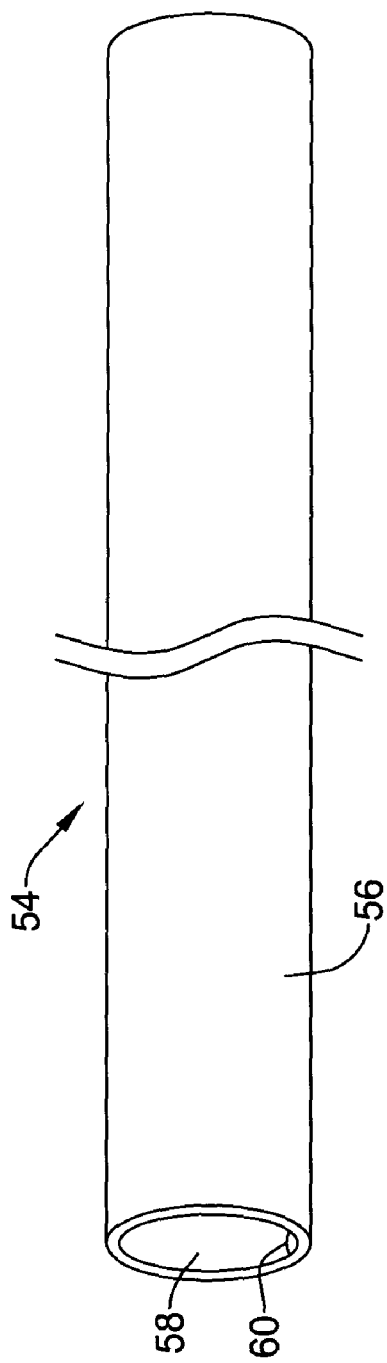
FIG. 7 is a side elevation view of a catheter in a deflated configuration, in accordance with an embodiment of the invention.

FIGS. 7 through 12 illustrate embodiments of the invention in which inflatable elements are deployed within catheters to provide for adjustable stiffness. In FIG. 7, a catheter 54 includes an elongate shaft 56. As discussed previously with respect to FIG. 1, the elongate shaft 56 may be a polymeric shaft and may include a single polymeric layer, two polymeric layers, or several polymeric layers, reinforcing layers, and the like. A lumen 58 extends through the interior of the elongate shaft 56, which can be formed of any suitable polymer or polymers.

An elongate inflation tube 60 is deployed within the lumen 58. In some instances, the elongate inflation tube 60 may be integrally formed within the elongate shaft 56. In some cases, the elongate inflation tube 60 may be separately formed and subsequently secured within the lumen 58 using any suitable attachment technique. As seen in FIG. 7, the elongate inflation tube 60 is deflated. The elongate inflation tube 60 can be formed of any suitable polymer or polymers.

Figure 8:
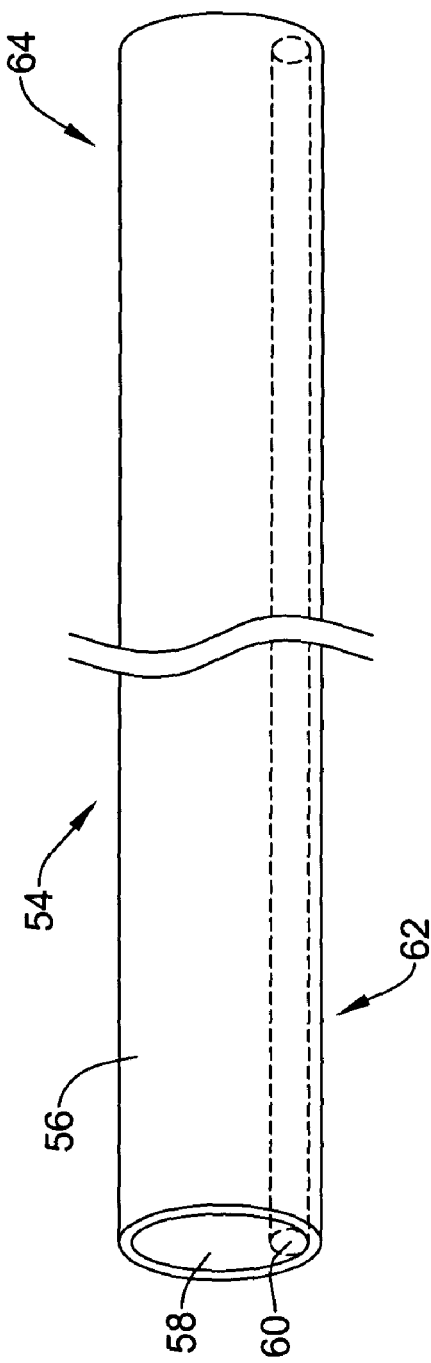
FIG. 8 is a side elevation view of the catheter of FIG. 7 in an inflated configuration, in accordance with an embodiment of the invention.

Turning to FIG. 8, the elongate inflation tube 60 has been inflated. The elongate inflation tube 60 can be seen as extending at least substantially the entire length of the elongate shaft 56, from a proximal region 62 to a distal region 64. In some instances, the elongate inflation tube 60 can be considered as extending proximally sufficiently far to be in fluid communication with the hub 22 (see FIG. 1), so that inflation fluid may be introduced into the elongate inflation tube 60. Any suitable fluid may be used, although saline is an exemplary fluid. Saline is biocompatible, which is important if a rupture occurs. Moreover, as an aqueous solution, saline is largely incompressible.

In the illustrated embodiment, the elongate inflation tube 60 has a radial cross-section that is at least substantially circular in shape, and that remains at least substantially constant across the length of the elongate inflation tube 60. In some instances, it is contemplated that the elongate inflation tube 60 may have a non-circular radial cross-section. For example, the elongate inflation tube 60 may have an ovoid or even polygonal radial cross-section.

In some instances, it is contemplated that the elongate inflation tube 60 may have a radial cross-section that changes size across the length thereof. For example, the elongate inflation tube 60 may have a smaller radial cross-section within the distal region 64 and a larger radial cross-section within the proximal region 62. In some instances, the elongate inflation tube 60 may have two, three or more distinct regions, each region having a distinctive radial cross-section size and/or shape.

It can be seen that the elongate inflation tube 60 can have relatively little impact on the flexibility of the elongate shaft 56 when deflated. When the elongate inflation tube 60 is inflated or pressurized, however, the elongate shaft 56 will become relatively less flexible, or relatively more stiff.

Figure 9:
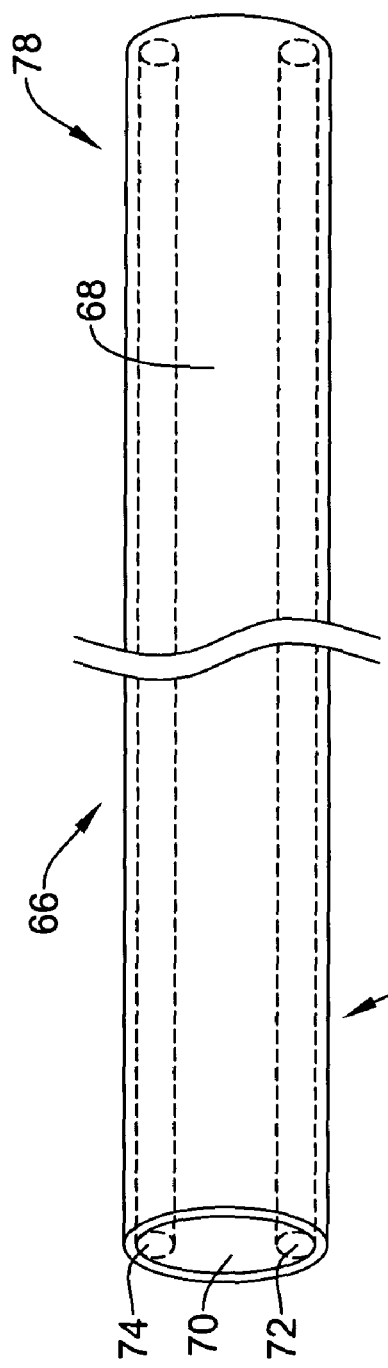
FIG. 9 is a side elevation view of a catheter in accordance with an embodiment of the invention.

FIG. 9 shows a catheter 66 that includes an elongate shaft 68. The elongate shaft 68 may be a polymeric shaft and may include a single polymeric layer, two polymeric layers, or several polymeric layers, reinforcing layers, and the like. A lumen 70 extends through the interior of the elongate shaft 68, which can be formed of any suitable polymer or polymers.

A first elongate inflation tube 70 and a second elongate inflation tube 72 are deployed within the lumen 70. In some instances, the first elongate inflation tube 70 and the second elongate inflation tube 72 may be integrally formed within the elongate shaft 68. In some cases, the first elongate inflation tube 70 and the second elongate inflation tube 72 may be separately formed and subsequently secured within the lumen 68 using any suitable attachment technique. Each of the first elongate inflation tube 70 and the second elongate inflation tube 72 may be formed of any suitable material.

As illustrated, the first elongate inflation tube 70 and the second elongate inflation tube 72 have been inflated or pressurized, and can be seen as being at least substantially parallel with each other. In some cases, the first elongate inflation tube 70 and the second elongate inflation tube 72 may be arranged at an angle with respect to each other. Each of the first elongate inflation tube 70 and the second elongate inflation tube 72 can be seen as extending at least substantially the entire length of the elongate shaft 68, from a proximal region 76 to a distal region 78.

In some instances, the first elongate inflation tube 70 and the second elongate inflation tube 72 can each be considered as extending proximally sufficiently far to be in fluid communication with the hub 22 (see FIG. 1), so that inflation fluid may be introduced. Any suitable fluid may be used, although saline is an exemplary fluid.

Figure 10:
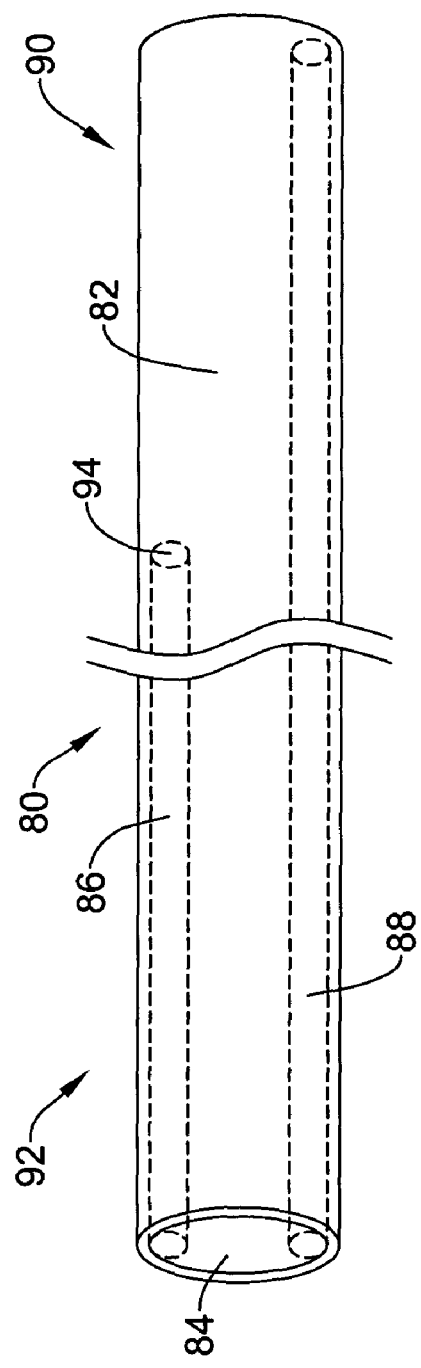
FIG. 10 is a side elevation view of a catheter in accordance with an embodiment of the invention.

In FIG. 10, a catheter 80 can be seen as including an elongate shaft 82. The elongate shaft 82 may be a polymeric shaft and may include a single polymeric layer, two polymeric layers, or several polymeric layers, reinforcing layers, and the like. A lumen 84 extends through the interior of the elongate shaft 82, which can be formed of any suitable polymer or polymers.

A first elongate inflation tube 86 and a second elongate inflation tube 88 are deployed within the lumen 84. In some instances, the first elongate inflation tube 86 and the second elongate inflation tube 88 may be integrally formed within the elongate shaft 82. In some cases, the first elongate inflation tube 86 and the second elongate inflation tube 88 may be separately formed and subsequently secured within the lumen 68 using any suitable attachment technique. The first elongate inflation tube 86 and the second elongate inflation tube 88 can be formed of any suitable polymer or polymers.

As illustrated, the first elongate inflation tube 86 and the second elongate inflation tube 88 have been inflated or pressurized. The second elongate inflation tube 88 can be seen as extending at least substantially the entire length of the elongate shaft 82, from a distal region 90 to a proximal region 92. The first elongate inflation tube 86, however, terminates at a position 94 that is well short of the distal region 90. In some instances, it may be desirable to be able to temporarily provide additional stiffness to the proximal region 92 while retaining a relatively greater level of flexibility within the distal region 90.

In some instances, the first elongate inflation tube 86 and the second elongate inflation tube 88 can each be considered as extending proximally sufficiently far to be in fluid communication with the hub 22 (see FIG. 1), so that inflation fluid may be introduced. Any suitable fluid may be used, although saline is an exemplary fluid.

Figure 11:
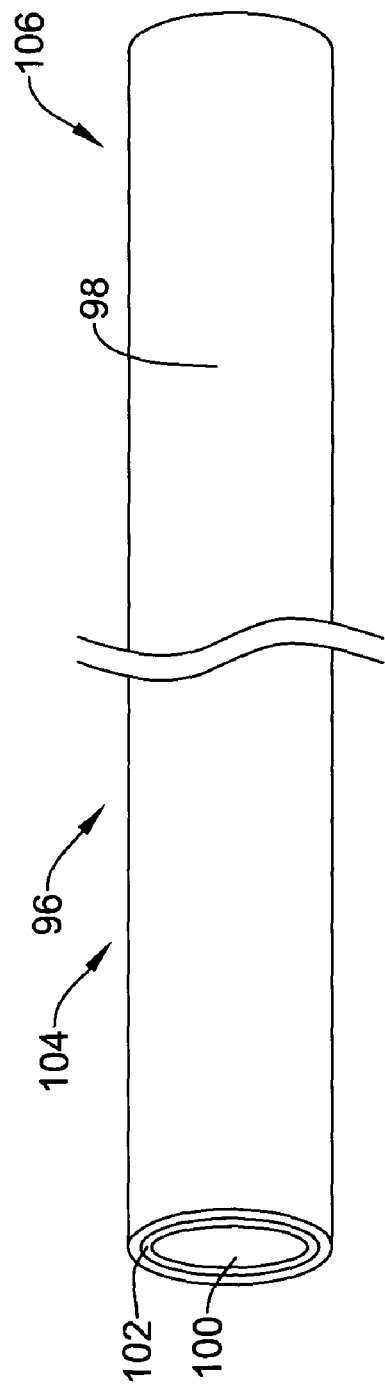
FIG. 11 is a side elevation view of a catheter in accordance with an embodiment of the invention.

FIG. 11 shows a catheter 96 having an elongate shaft 98. The elongate shaft 98 may be a polymeric shaft and may include a single polymeric layer, two polymeric layers, or several polymeric layers, reinforcing layers, and the like. A lumen 100 extends through the interior of the elongate shaft 98, which can be formed of any suitable polymer or polymers.

An elongate annular inflation ring 102 is deployed within the lumen 100. In some instances, the elongate annular inflation ring 102 may be integrally formed within the elongate shaft 98. In some cases, the elongate annular inflation ring 102 may be separately formed and subsequently secured within the lumen 100 using any suitable attachment technique. The elongate annular inflation ring 102 can be formed of any suitable polymer or polymers.

As seen, the elongate annular inflation ring 102 is inflated or pressurized. The elongate annular inflation ring 102 can extend at least substantially the entire length of the elongate shaft 98, from a proximal region 104 to a distal region 106. In some instances, the elongate annular inflation ring 102 can be considered as extending proximally sufficiently far to be in fluid communication with the hub 22 (see FIG. 1), so that inflation fluid may be introduced into the elongate annular inflation ring 102. Any suitable fluid may be used, although saline is an exemplary fluid.

Figure 12:
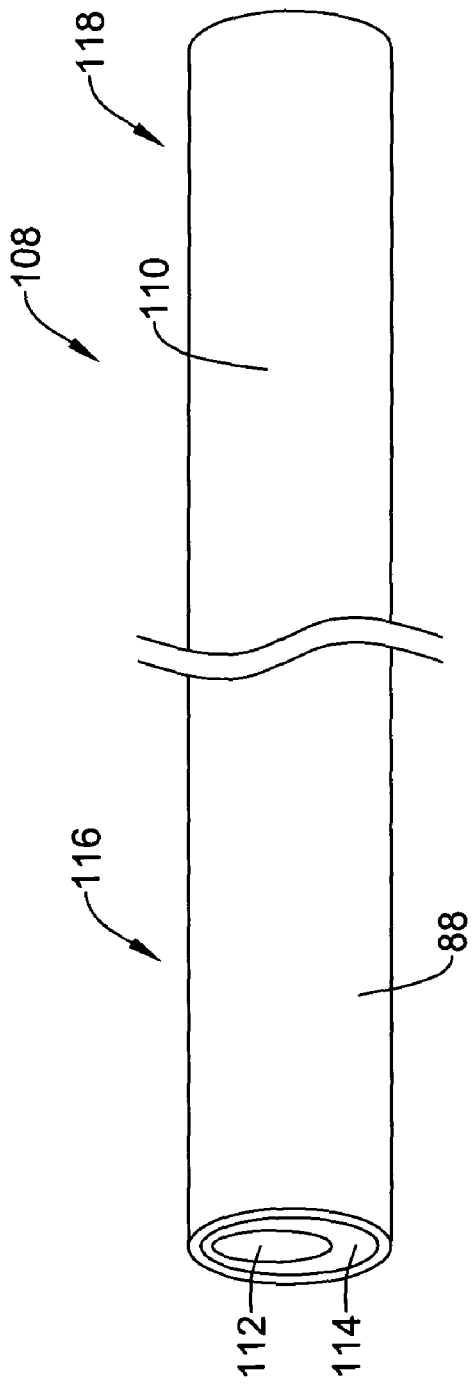
FIG. 12 is a side elevation view of a catheter in accordance with an embodiment of the invention.

FIG. 12 shows a catheter 108 having an elongate shaft 110. The elongate shaft 110 may be a polymeric shaft and may include a single polymeric layer, two polymeric layers, or several polymeric layers, reinforcing layers, and the like. A lumen 112 extends through the interior of the elongate shaft 110, which can be formed of any suitable polymer or polymers.

An elongate inflation ring 114 is deployed within the lumen 112. In some instances, the elongate inflation ring 114 may be integrally formed within the elongate shaft 110. In some cases, the elongate inflation ring 114 may be separately formed and subsequently secured within the lumen 112 using any suitable attachment technique. The elongate inflation ring 114 can be formed of any suitable polymer or polymers.

The elongate annular inflation ring 102 (FIG. 11) has at least a substantially constant dimension. In contrast, the elongate inflation ring 114 has a varying dimension. In some instances, the elongate inflation ring 114 can have a relatively thinner dimension along one side (top, as illustrated) and a relatively thicker dimension along another side (bottom, as illustrated). This can be useful if it is desired to provide relatively greater stiffness along one side of the catheter 108 and relatively reduced stiffness along another side of the catheter 108.

As seen, the elongate inflation ring 114 is inflated or pressurized. The elongate inflation ring 114 can extend at least substantially the entire length of the elongate shaft 110, from a proximal region 116 to a distal region 118. In some instances, the elongate inflation ring 114 can be considered as extending proximally sufficiently far to be in fluid communication with the hub 22 (see FIG. 1), so that inflation fluid may be introduced into the elongate inflation ring 114. Any suitable fluid may be used, although saline is an exemplary fluid.

Figure 13:
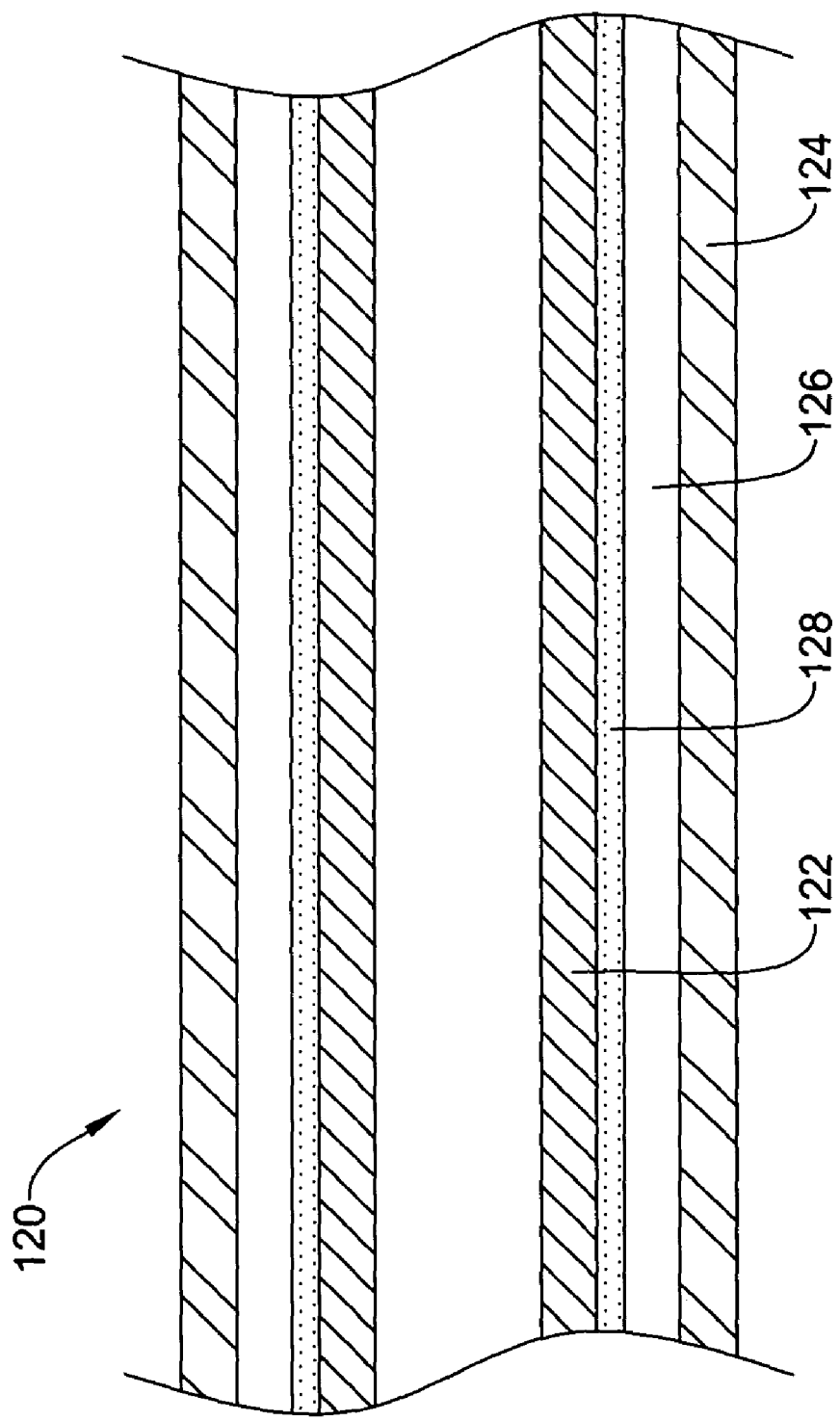
FIG. 13 is a diagrammatic longitudinal cross-section of a catheter in accordance with an embodiment of the invention.
Figure 14:
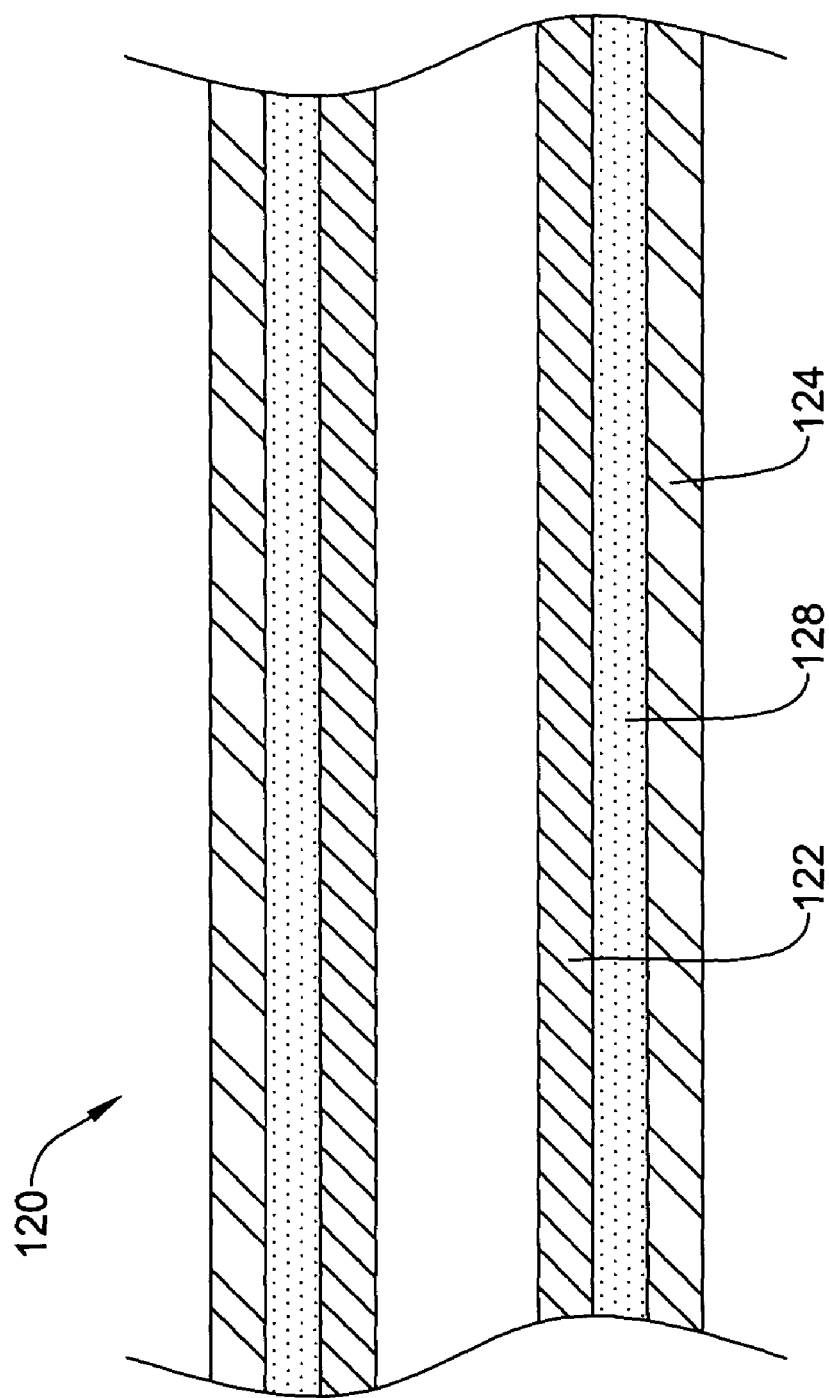
FIG. 14 is a view of the catheter of FIG. 13.

FIGS. 13 and 14 illustrate an embodiment in which a swellable material such as a hydrogel is used to provide a catheter with adjustable stiffness. In FIG. 13, a portion of a catheter 120 includes an inner polymer layer 122 and an outer polymer layer 124. The inner polymer layer 122 and the outer polymer layer 124 can each independently be formed of any suitable polymer or polymers. A gap 126 is disposed between the inner polymer layer 122 and the outer polymer layer 124. A layer or coating 128 of a swellable material is disposed within the gap 126. As seen in this Figure, the coating 128 is dry.

In FIG. 14, the coating 128 of swellable material has been caused to swell, thereby eliminating the gap 126 seen in FIG. 13. The coating 128 can be caused to swell by contacting the coating 128 with an appropriate liquid. If, for example, the coating 128 is a hydrogel, it can be caused to swell simply by contacting the coating 128 with water. In some instances, the gap 126 (FIG. 13) can be considered as extending proximally sufficiently far to be in fluid communication with the hub 22 (see FIG. 1), so that an appropriate liquid such as water may be introduced.

Examples of suitable swellable materials include hydrophilic polymers. A hydrophilic polymer is a polymer that attracts or binds water molecules when the polymer is placed in contact with an aqueous system. Examples of aqueous systems that can provide water molecules that can bind to a hydrophilic polymer include blood and other bodily fluids. When a hydrophilic polymer comes into contact with such a system, water molecules can bind to the polymer via mechanisms such as hydrogen bonding between the water molecules and substituents or functional groups present within or on the polymer.

One class of polymers that can be considered as hydrophilic includes ionomer polymers. An ionomer polymer is a polymer that can be considered as containing covalent bonds between elements within a chain while containing ionic bonds between chains. An ionomer polymer is a polymer that has charged functional groups appended to the polymer chain. The charged functional groups can be positively charged, in which case the polymer can be referred to be a cationomer, or the functional groups can be negatively charged, in which case the polymer can be referred to as an anionomer.

An ionomeric polymer can be formed using a variety of negatively charged functional groups. The negatively charged functional group can be added to a previously formed polymer, or the negatively charged functional groups can be part of one or more of the monomers used to form the ionomeric polymer.

Examples of suitable negatively charged functional groups include sulfonates and carboxylates. The ionomeric polymer can, in particular, include sulfonate functional groups. These groups are negatively charged and can readily hydrogen bond sufficient amounts of water when brought into contact with a source of water such as an aqueous system.

Further examples of suitable materials include nonionic polyether polyurethanes available commercially under the HYDROSLIP® name. Another suitable material includes nonionic aliphatic polyether polyurethanes available commercially under the TECOGEL® name. Examples of other suitable nonionic polymers include polymers such as poly (hydroxy methacrylate), poly (vinyl alcohol), poly (ethylene oxide), poly (n-vinyl-2-pyrolidone), poly (acrylamide) and other similar materials.

Figure 17:
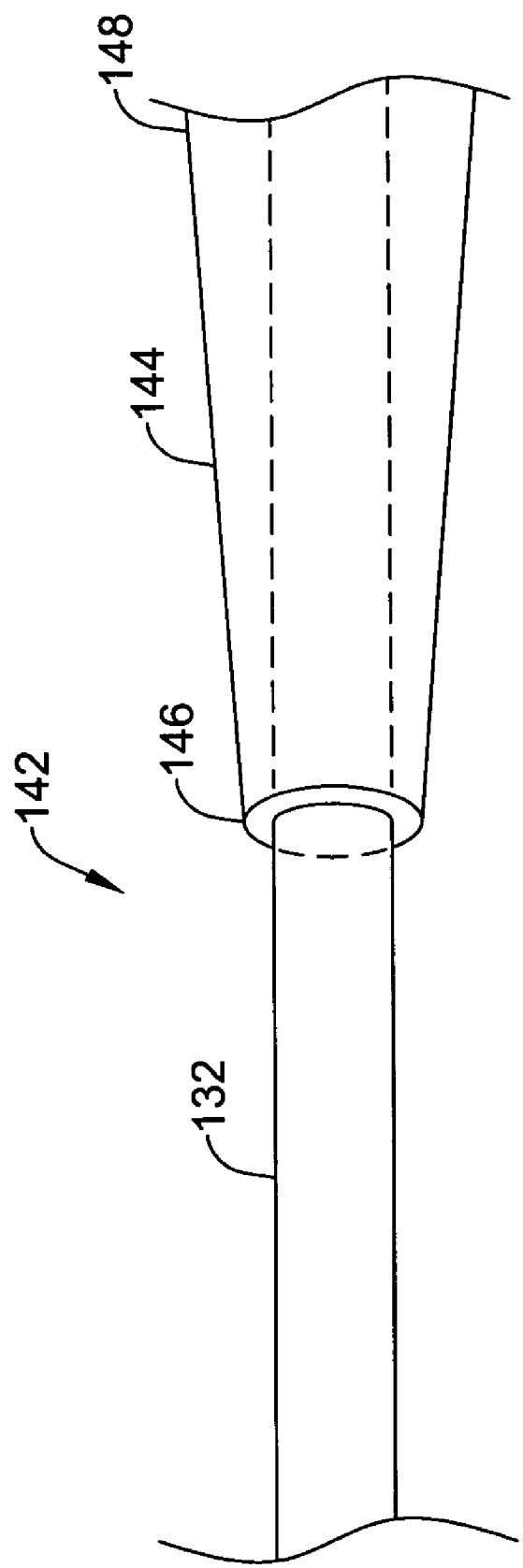
FIG. 17 is a side elevation view of a catheter in accordance with an embodiment of the invention.

FIGS. 15 through 17 illustrate embodiments of the invention in which catheters can enjoy adjustable stiffness through the use of external sheaths that may be slidably disposed over the catheters.

FIG. 15 shows a catheter 130 including an elongate shaft 132 and a stiffness sheath 134 slidably disposed over the elongate shaft 132. The elongate shaft 132 may be a polymeric shaft and may include a single polymeric layer, two polymeric layers, or several polymeric layers, reinforcing layers, and the like. Any suitable polymer or polymers can be used. The stiffness sheath 134 may be formed of any suitably stiff polymeric or metallic material.

In FIG. 16, a catheter 136 includes the elongate shaft 132 as discussed with respect to FIG. 15. A first stiffness sheath 138 is slidably disposed over the elongate shaft 132, while a second stiffness sheath 140 is slidably disposed over the first stiffness sheath 138. In some instances, each of the first stiffness sheath 138 and the second stiffness sheath 140 may independently be moved either distally or proximally over the elongate shaft 132 to provide a desired degree of stiffness. Each of the first stiffness sheath 138 and the second stiffness sheath 140 may be formed of any suitably stiff polymeric or metallic material.

In FIG. 17, a catheter 142 includes the elongate shaft 132 as discussed with respect to FIG. 15. A tapered or frustoconical-shaped stiffness sheath 144 is slidably disposed over the elongate shaft 132. The stiffness sheath 144 has a narrow end 146 and a wide end 148 and can provide, as a result, a gradual change in stiffness. The stiffness sheath 144 can be formed of any suitably stiff polymeric or metallic material.

Figure 18:
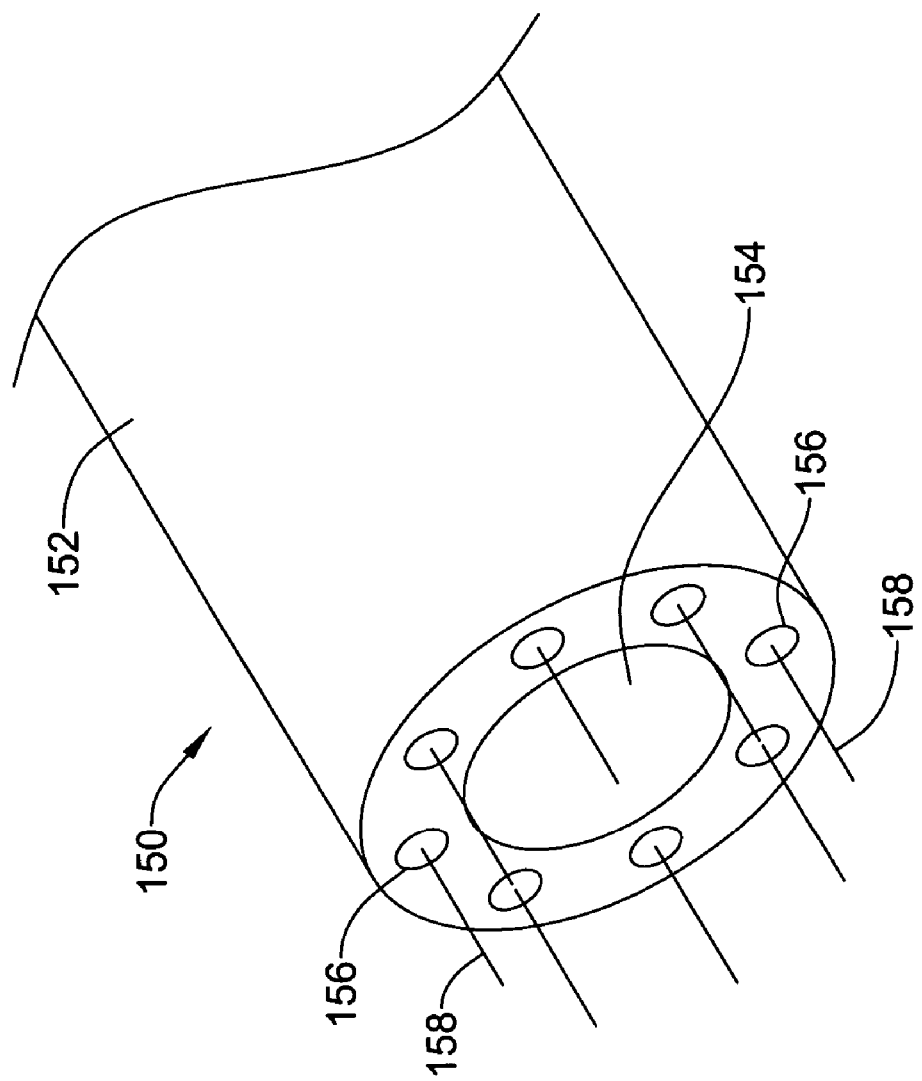
FIG. 18 is a perspective view of a catheter in accordance with an embodiment of the invention.

FIG. 18 illustrates an embodiment of the invention employing a number of stiffness filaments. A catheter 150 includes an elongate shaft 152. The elongate shaft 152 may be a polymeric shaft and may include a single polymeric layer, two polymeric layers, or several polymeric layers, reinforcing layers, and the like. A lumen 154 extends through the elongate shaft 152, which can be formed of any suitable polymer or polymers.

The catheter 150 includes a number of elongate apertures 156 disposed within the elongate shaft 152. It can be seen that the elongate apertures 156 extend longituidinally within the elongate shaft 152. The elongate apertures 156 can be evenly spaced out about the circumference of the elongate shaft 152. Any number of elongate apertures 156 may be provided. At least some of the elongate apertures 156 include a stiffness-enhancing filaments 158 slidably deployed within the elongate apertures 156.

Depending on the performance requirements, one or more of the stiffness-enhancing filaments 158 may be inserted into, removed from, or slide within an appropriate and corresponding elongate aperture 156. In some instances, the stiffness-enhancing filaments 158 may be wires formed of any suitable material such as Nitinol, stainless steel, titanium, aluminum, cobalt chromium or any other suitable metal.

Figure 19:
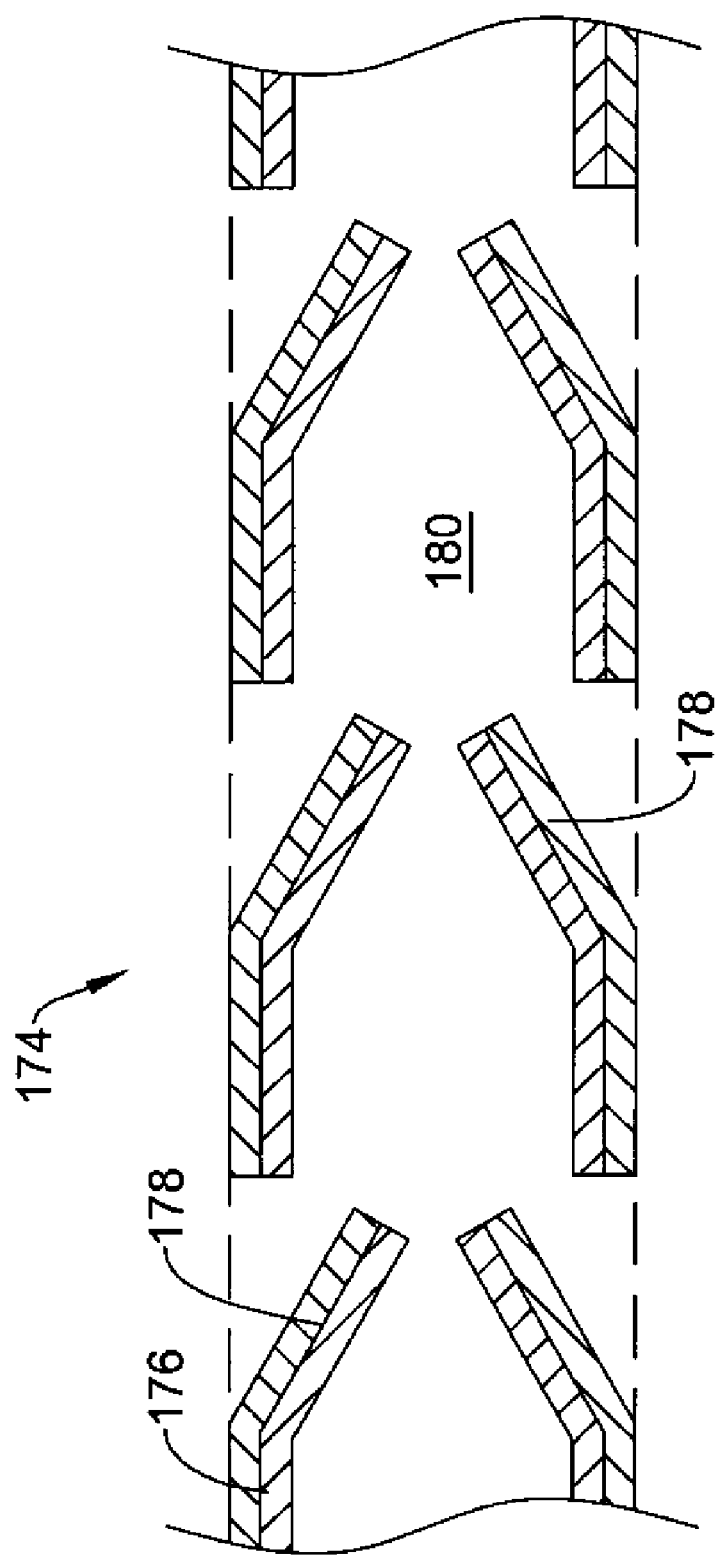
FIG. 19 is a diagrammatic longitudinal cross-section of a catheter in a relaxed configuration, in accordance with an embodiment of the invention.
Figure 20:
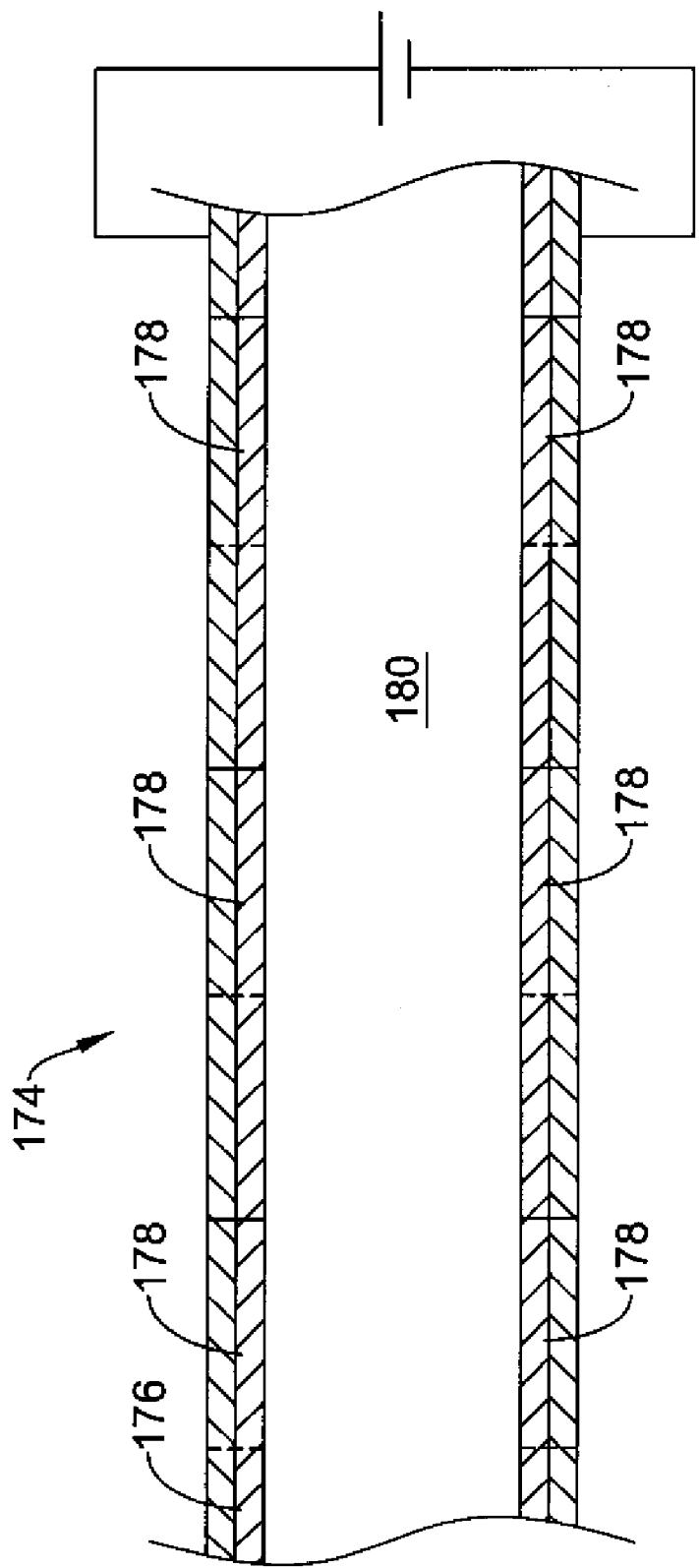
FIG. 20 is a view of the catheter of FIG. 19 in an actuated configuration, in accordance with an embodiment of the invention.

FIGS. 19 and 20 illustrate use of an electro-active polymer in providing variable stiffness to a catheter. FIG. 19 shows a catheter 174 having an elongate shaft 176 that includes one or more polymeric layers. A series of flaps 178 have been cut into the elongate shaft 176, and extend into a lumen 180. At least the flaps 178 include an electro-active polymer. It should be noted that the size of the flaps 178 relative to the elongate shaft 176 has been exaggerated for illustrative purposes. In this configuration, which can be considered to be a relaxed configuration, the flaps 178 provide a level of flexibility to the elongate shaft 176.

In FIG. 20, a current has been applied. Consequently, the flaps 178 have been actuated from the position seen in FIG. 19, in which the flaps 178 extend into lumen 180, to a position in which the flaps 178 align with the elongate shaft 176 and thereby improve the column strength of the elongate shaft 176.

It should be noted that in some instances, it is contemplated that at least a portion of elongate shaft 12 (see FIG. 1) may be formed from or include a layer of an electrostatically actuatable material such as an electro-active polymer, a polymer including buckytubes, or perhaps a liquid crystal polymer. It is contemplated that such materials may, if subjected to an electrical current, change the relative stiffness of a catheter containing such a material.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

We claim:

1. An adjustable catheter, the catheter having a distal region and a proximal region, the catheter comprising:
   an inner polymeric layer comprising one or more electrically actuated column stiffness enhancers, the inner polymeric layer defining a lumen, the inner polymeric layer including an outer surface; and
   an outer polymeric layer disposed over the inner polymeric layer,
   wherein the one or more electrically actuated column stiffness enhancers may be actuated by applying a current thereto;
   wherein the one or more electrically actuated column stiffness enhancers comprise polymeric flaps having a relaxed position in which the polymeric flaps extend into the lumen and an actuated position in which the polymeric flaps align with the outer surface of the inner polymeric layer.

2. The adjustable catheter of claim 1, wherein the one or more electrically actuated column stiffness enhancers comprise an electroactive polymer.

3. The adjustable catheter of claim 1, wherein the catheter has a column stiffness and actuating the column stiffness enhancers changes the column stiffness of the catheter.

4. The adjustable catheter of claim 1, wherein the one or more electrically actuated column stiffness enhancers comprise a polymer including buckytubes.

5. The adjustable catheter of claim 1, wherein the one or more electrically actuated column stiffness enhancers comprise a liquid crystal polymer.

* * * * *